United States Patent
Pokorny et al.

(10) Patent No.: US 7,445,440 B2
(45) Date of Patent: Nov. 4, 2008

(54) POLYMERIZATION TEMPERATURE TEST ELEMENT

(75) Inventors: Walter Pokorny, Thuringen (AT); Michael Brotzge, Koblach (AT); Werner Langle, Frastanz (AT); Werner Kindle, Vaduz (LI)

(73) Assignee: Ivoclar Vivadent A.G., Schaan (LI)

( * ) Notice: Subject to any disclaimer, the term of this patent is extended or adjusted under 35 U.S.C. 154(b) by 682 days.

(21) Appl. No.: 10/622,419

(22) Filed: Jul. 18, 2003

(65) Prior Publication Data

US 2004/0175293 A1 Sep. 9, 2004

(30) Foreign Application Priority Data

Mar. 6, 2003 (DE) .................... 103 09 855

(51) Int. Cl.
*B29C 35/02* (2006.01)

(52) U.S. Cl. .............. 425/170; 249/54; 425/174.4

(58) Field of Classification Search ............... 425/169, 425/174.4, 170, 171, 173; 264/40.6, 16; 116/216; 219/720; 374/162
See application file for complete search history.

(56) References Cited

U.S. PATENT DOCUMENTS

| | | | |
|---|---|---|---|
| 3,816,264 A | 6/1974 | Winter et al. | |
| 4,015,591 A | 4/1977 | Suzuki et al. | |
| 4,786,773 A | 11/1988 | Keefer | |
| 4,793,717 A | 12/1988 | Manske | |
| 4,871,674 A | 10/1989 | Matsui et al. | |
| 4,933,525 A * | 6/1990 | St. Phillips | 219/725 |
| 5,667,303 A * | 9/1997 | Arens et al. | 374/102 |
| 5,720,555 A * | 2/1998 | Elele | 374/150 |
| 5,786,578 A * | 7/1998 | Christy et al. | 219/720 |
| 5,922,605 A | 7/1999 | Feurstein et al. | |
| 6,386,756 B1 | 5/2002 | Rice | |
| 6,467,953 B1 * | 10/2002 | Faries et al. | 374/162 |
| 6,694,638 B1 * | 2/2004 | Krioukov et al. | 34/89 |
| 2004/0240520 A1 * | 12/2004 | Faries et al. | 374/162 |
| 2006/0137368 A1 * | 6/2006 | Kang et al. | 62/149 |

FOREIGN PATENT DOCUMENTS

| | | |
|---|---|---|
| DE | 15 98 308 | 10/1969 |
| DE | 24 14 781 | 10/1975 |
| DE | 69617539 T2 | 1/1997 |
| DE | 196 18 542 | 11/1997 |
| DE | 198 09 318 C1 | 5/1999 |
| DE | 199 50 516 A1 | 4/2001 |
| EP | 0 329 579 | 8/1989 |

* cited by examiner

*Primary Examiner*—Yogendra Gupta
*Assistant Examiner*—Emmanuel S Luk
(74) *Attorney, Agent, or Firm*—John C. Thompson; Alan S. Korman

(57) ABSTRACT

A polymerization temperature test element is provided for a polymerization device of the type, in particular, for polymerizing dental products. The polymerization temperature test element includes a base element and a receipt region centrally disposed on the base element and operable to receive the mass to be polymerized. The energy source of the polymerization device irradiates the mass to be polymerized with one or both of light radiation and thermal radiation to effect polymerization of the mass and the base element and the receipt region are configured so as to be subjected to the respective light and thermal radiation emitted by the energy source. Accordingly, the polymerization temperature test element provides an indication, via color-temperature indicators which change color or brightness at discrete temperatures, that a target polymerization temperature has been reached during irradiation of the mass.

5 Claims, 3 Drawing Sheets

Fig. 5
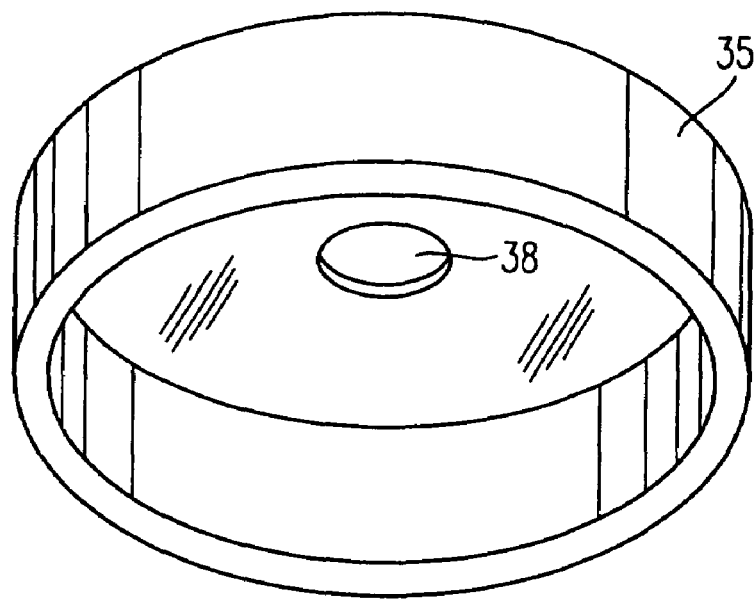
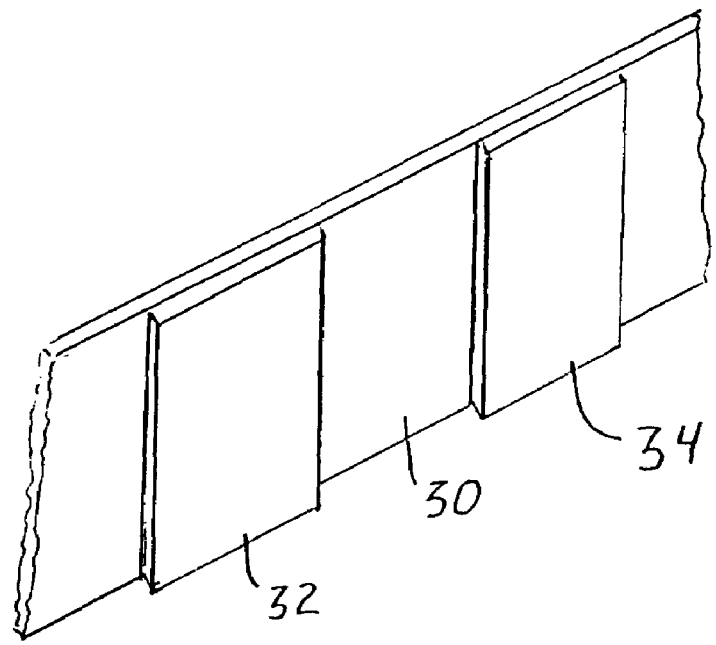
Fig. 6

POLYMERIZATION TEMPERATURE TEST ELEMENT

CROSS-REFERENCE TO RELATED APPLICATIONS

This application claims foreign priority benefits under 35 U.S.C. §119(a)-(d) from German patent application ser. no. P 103 09 855.0 filed Mar. 6, 2003.

TECHNICAL FIELD

The present invention relates to a polymerization temperature test element and, in particular, a polymerization temperature test element for indicating that a target polymerization temperature has been reached.

BACKGROUND

It is known that polymerization devices such as, for example, light polymerization devices, are used for polymerizing restoration materials such as, for example, materials in dental products, and require an exact output of the polymerization radiation in order to ensure a reliable and reproducible restoration result. It is known that a deviation from the pre-set irradiation value can lead to significant degradation of restoration results. Thus, an overly intensive energy irradiation leads to an overly strong complete hardening and, consequently, edge crack formation, while an overly minimized energy irradiation leads to an incomplete hardening so that there remains a not-polymerized monomer portion in the dental restoration.

Polymerization devices for dental practices are frequently operated at various radiation frequency spectrums. Thus, it is known to integrate thermal sources as well as light sources in the hood of a polymerization device. A solution of this type is disclosed, for example, in U.S. Pat. No. 5,922,605.

Various measures have been suggested for calibrating the light output of halogen light sources. Thus, it has been suggested to dispose a light sensor at a precisely determined distance from the light source with the light sensor having a pre-determined spectral sensitivity. The output signal of the light sensor should then indicate the light intensity of the light source reaching the location of interest.

A solution of this type requires, to be sure, a corresponding switch connection for the outputs of the light sensor. On the other hand, a mobile wiring arrangement for a light sensor—which must then be removed in operation—when combined with a corresponding switch, is significantly expensive and, also, is susceptible to errors. Care must be taken with such an arrangement that, for example, it is not overlooked, during the light measurement operation, that the thermal source is inadvertently actuated as otherwise the light sensor will, in such a situation, be subjected to damage.

Current combined thermal and light hardening devices emit, to a large extent, infrared radiation—that is, thermal radiation—in order to effect the polymerization. This means, on the one hand, that the infrared radiation must be at least as significant as the light radiation, if not even more significant. On the other hand, in connection with the construction of such combined thermal and light polymerization devices, it has consistently been assumed that a commercially available thermostat is adequate for a workably precise determination of the temperature. A thermostat of this type can be configured in classic manner with the use of a bimetallic strip, or configured in electronic configuration—that is, via the use of a PTC—or, optionally, an NTC—, resistance element. Such thermostats are calibrated and it is assumed that the precision during the operational life of the device is adequate.

On the other hand, the materials used for the production of temperature sensors typically exhibit a certain degree of aging. In order to compensate for such aging, it is recommended that a re-calibration be performed. For example, a mobile electronic and calibrated temperature calibration unit provided with a sensor, which is mounted on the tip of a probe, is inserted in the polymerization device between the base and hood thereof in order to undertake a re-calibration. Such a re-calibration arrangement can, however, for all practical purposes, only be provided by the producer of the polymerization device, as the customers of the polymerization devices would not be motivated to procure such a significantly expensive electronic temperature calibration unit.

SUMMARY OF THE INVENTION

The present invention provides a solution to the challenge of providing a polymerization device and/or a polymerization temperature test element which provides an improved reliability of the polymerization accomplished by polymerization devices without otherwise requiring a special effort to achieve such an improved reliability.

In accordance with the present invention, it is particularly advantageous if a polymerization temperature test element is deployed in the polymerization device and comprises a base element having a receipt region on which the mass to be polymerized is disposed. By virtue of these surprisingly simple measures, the possibility is provided to irradiate the polymerization temperature test element with radiation from the thermal source and/or the light source of the polymerization device and, in this manner, to monitor the extent to which the actual polymerization result corresponds to the expected polymerization result.

In a particularly advantageous embodiment of the present invention, the polymerization temperature test element is connected with a plurality of covered color-temperature indicators which permit the recognition of a color conversion which occurs at a certain pre-determined temperature. The temperature indicators can be arranged in the manner of a scale, so that the color conversion precisely corresponds to the achieved temperature. The monitoring is promoted by the provision of an irreversible color change. Corresponding temperature indicators are disclosed, for example, in DE-OS 199 50 516, as well as U.S. Pat. No. 4,015,591.

In accordance with the present invention, it is particularly advantageous that the polymerization temperature test element is provided with means for establishing, at a certain pre-determined adjustment, the hardening depth of the material to be polymerized. This hardening depth of the material to be polymerized can be established either by measurement of the hardening border of the material removed from the receipt region or via determination of the temperature, such as, for example, via the change of color of the color-temperature indicators of the present invention.

The deployment of a polymerization temperature test element of this type as the test device has the advantage that the capital costs can be kept to a low amount. The base element need only comprise an adequate temperature stability of, for example, 150° C. The temperature indicators can be mounted in cost-favorable manner in strip form on the inner peripheral wall, whereby such strip-shaped temperature indicators can be produced in a cost-favorable manner.

In a particularly advantageous embodiment of the present invention, the base element has a light blocking coating which prevents passage therethrough of the respective light irradiation lying in the radiation region of the polymerization device. If the operational setting of the base element is chosen such that a light covering of the temperature indicators is provided, this configuration forecloses the possibility that the light irradiation will produce a false measurement of the temperature. For example, the polymerization temperature test element can be substantially shell-shaped and then can be mounted in a reversed manner on the planar base surface of the polymerization device. The polymerization temperature test element protects, at least, the inner or outer mounted strips of the temperature indicators, if the device includes a substantially planer base wall.

It is to be understood that other desired types of coverings are possible. For example, during the irradiation of, as well, the base element, a type of hood can be disposed thereover which performs the desired shielding against radiation and which can be removed after the measurement process.

It is easy to determine the deviation from the given temperature via close-up inspection of the color change of the temperature indicators and a re-adjustment or calibration of the polymerization device can be undertaken without further accommodation via, for example, a calibration potentiometer mounted in a covered manner.

In accordance with the present invention, it is particularly advantageous that the inventive polymerization temperature test element is disposed exactly at the location in which the restoration piece is to be polymerized during the operation. In this manner, a precise temperature establishment can be undertaken.

It is to be understood that, in accordance with the present invention, a calibration of the polymerization device at several calibration points is possible with a polymerization temperature test element. In this connection, serially different temperatures are inputted as given temperatures and, upon the reaching of the relevant end temperatures, the color-temperature indicator, which corresponds to the respective temperature, is visually observed and the occurrence of deviations is established.

It is to be understood, that, in connection with this solution, it is meaningful to undertake an establishment of the rising calibration temperatures, at least if irreversible color-temperature indicators are used.

Via the inventive shielding against the irradiation, it is ensured, at the same time, that the energy sources of the polymerization device do not emit any radiation energy onto the temperature indicator, which would otherwise cause a falsification of the temperature measurement result.

In an advantageous embodiment of the present invention, it is provided that an area of the polymerization device which extends intermediate the energy source and the color-temperature indicator is impermeable to the respective radiation emitted from the energy source lying in the spectral region of the energy source.

It is particularly advantageous if the color-temperature indicator or the color-temperature indicators are configured on the open surfaces of the base element which are downwardly oriented or on the open surfaces which are inwardly oriented and opening downwardly.

In an advantageous embodiment of the present invention, it is provided that a protection foil is disposed on the polymerization temperature test element which covers the material to be polymerized disposed at the receipt region. The protection foil protects the material from a premature hardening, which would otherwise lead to falsification of the measurement result. At the same time, it is possible to make ready a particularly smooth over surface via the protective foil, which leaves a surface of such smoothness after its removal.

Additionally, although separate light sources and thermal sources have been described hereinabove, it is to be understood that the inventive approach can also be deployed with those polymerization devices which combine the light and thermal sources into one energy source, especially in connection with relatively older polymerization devices of this type. Precisely in such configurations, it can be determined whether the energy source still offers adequate performance or whether an exchange thereof is due.

In a particularly advantageous embodiment of the present invention, the base element is configured in a short cylindrical shape. The base element can be configured, for example, as a single integral piece and forms, together with the mass to be polymerized which is received in the receipt region, and, optionally, with the temperature indicators of the polymerization temperature test element, the polymerization temperature test element which, in its delivery condition to the user—that is, before its operational use—still has a light impermeable foil covering the receipt region.

The receipt region can preferably be in the form of a hub of the base element. It is preferred that the removable foil at least covers the outer surface of the receipt region which is operable to receive thereon the material to be polymerized. If the receipt region extends through the base element to function as a throughbore receipt region, it is correspondingly preferred that both sides (ends) of the throughbore receipt region are covered. If, on the other hand, the receipt region is configured in the manner of a bore with one closed end, solely the open end thereof is covered.

In a modified embodiment of the present invention, a light impermeable foil extends over the open side of the base element—that is, the side of the base element which is open toward the temperature indicators. A foil of this type serves, as well, to protect the temperature indicators during transport of the polymerization temperature test element.

The foils or foil are preferably mounted via a weld connection in conventional manner to the base element. The provision of a conventional grip handle permits removal of the foil without further additional removal structure. Via the weld connection, the penetration of adhesive material is prevented, which could otherwise negatively influence the temperature indicators and/or the polymerizable mass.

Further advantages, details, and features of the present invention, are described in the hereinafter following description of two embodiments of the present invention, taken in consideration with the figures of the drawing.

BRIEF DESCRIPTION OF THE FIGURES

FIG. 5 is a perspective view of a cover for a polymerization temperature test element of the present invention; and FIG. 6 is an enlarged view of color-temperature indicators mounted on a strip support element.

DETAILED DESCRIPTION OF THE PREFERRED EMBODIMENTS

Figure 1:
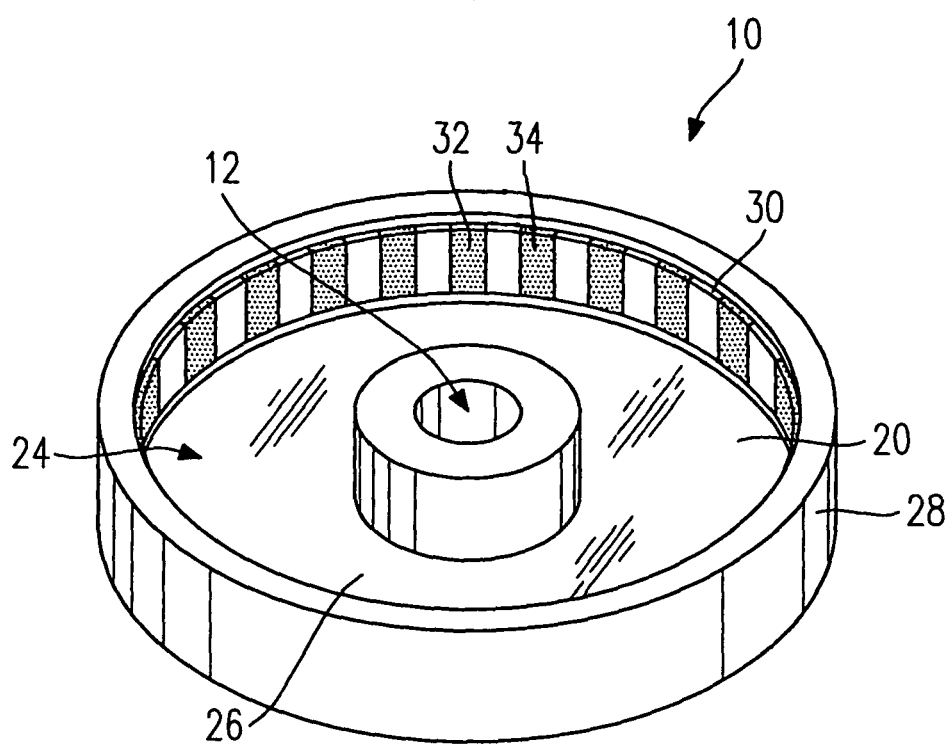
FIG. 1 is a perspective view of a first embodiment of the inventive base element.

The polymerization temperature test element shown in FIG. 1 is indicated generally at 10. It is configured specifically for a polymerization device. The polymerization device comprises a receipt area for receiving a restoration piece to be polymerized, which piece is not herein illustrated. A polymerization device can be used whose energy source is integrated in a hood which, in its lowered condition, encloses a restoration piece disposed on a planar base. In this connection, U.S. Pat. No. 5,922,605 is fully incorporated herein by reference thereto. It is also possible to deploy a polymerization device whose polymerizing effect is reinforced by overpressure.

The polymerization temperature test element comprises a central receipt region 12. In the first embodiment illustrated in FIGS. 1 and 2, the receipt region 12 is configured as a short cylinder and is configured in the manner of a centrally disposed hub. It is to be understood that the receipt region can be configured on any desired suitable location. For example, the receipt region can be annularly-shaped or a plurality of small receipt regions can extend from suitable locations, each of which can also receive a respective different material. The various polymerizing properties can be taken into account by such a configuration with respect to the different materials to be used.

In the first embodiment of the present invention, the receipt region 12 is cylindrically-shaped. Its opening, which is indicated generally at 14, can be better seen in FIG. 2, and extends, in this illustration, below or behind the plane of the drawing shown in FIG. 1. The receipt region 12 permits a mass to be disposed thereon which can be polymerized via light and/or thermal and/or pressure treatment. A radiation impermeable foil 16 covers the opening 14. The foil 16 is connected along an annular shaped welding bead 18 with the base element 20. A pull tab 23 facilitates, in conventional manner, the pulling-off of the foil 16.

The base element 20—excepting the receipt region 12—is, in any event, bowl-shaped. Its opening, which is indicated generally at 24, is arranged oppositely to the opening 14, such that the opening 24, in the first embodiment shown in FIG. 1, is open toward the top or front. The base element 20 comprises a base plate having a floor surface 26, the base plate being in an annular shape, and which is circumferentially enclosed at its outer edge by a circumferential wall 28.

A strip support element 30, comprised of paper, is mounted on the inner side of the circumferential wall 28. As can best be seen from FIG. 6, the strip support element 30 supports a plurality of color-temperature indicators of which two color-temperature indicators 32 and 34 are representatively illustrated. The pair of color-temperature indicators 32 and 34 are configured of a material whose brightness and/or color changes upon the reaching of a predetermined release temperature unique to the respective color-temperature indicator and, indeed, changes irreversibly. The color of the color-temperature indicator 32 may change from white to black at a temperature of 102° C. and the color-temperature indicator 34 may change its color from white to black upon reaching the temperature 106° C. In corresponding manner, those color-temperature indicators adjacent the color-temperature indicators 32 and 34 also each have respective unique release temperatures and the release temperatures preferably increase at a uniform temperature gradation. The strip support element 30 thus builds, together with the color-temperature indicators, a type of scale. Additionally, in the base area—that is, on the base plate 26—each color-temperature indicator can have its respective release temperature printed thereon; thus, the temperature 102° C. can be printed adjacent the color-temperature indicator 32 and the temperature 106° C. can be printed adjacent the color-temperature indicator 34.

Figure 2:
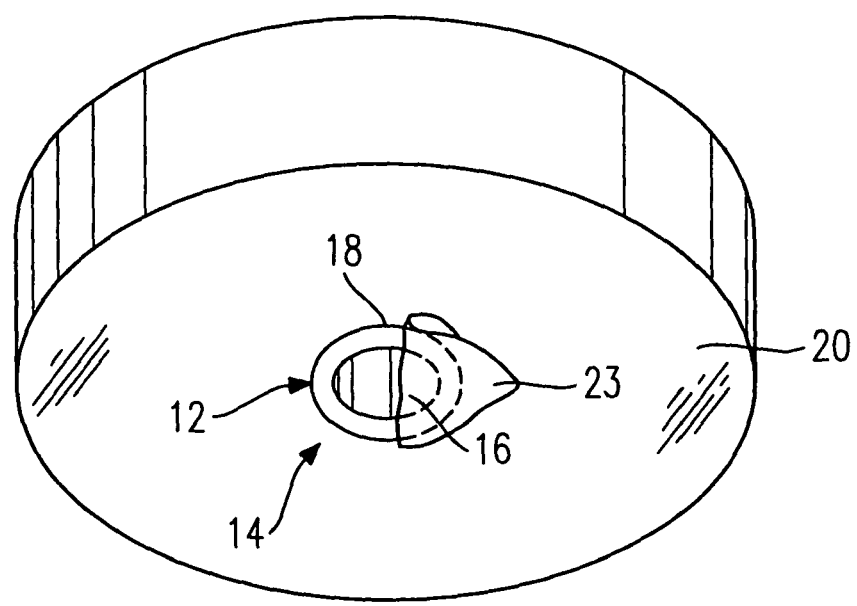
FIG. 2 is a view of the one embodiment of the polymerization temperature test element shown in FIG. 1.

In the first embodiment illustrated in FIGS. 1 and 2, a plurality of adjacently arranged color-temperature indicators are provided. In practice, up to 20 and even more color-temperature indicators can be finely classified (relatively small temperature gradations) or, alternatively, can be classified at relatively large scale temperature gradations, in correspondence with the respective desired employment thereof. It is to be understood, that due to cost reasons, in lieu of a multiplicity of color-temperature indicators, only a few color-temperature indicators or, in individual situations, solely two color-temperature indicators, can be deployed if the decision involved is simply whether the respective energy source of the polymerization device to be monitored—, typically, a lamp—is still able to, or not able to, provide an irradiation performance which results in a pre-set target temperature.

If the inventive polymerization temperature test element in the position shown in FIG. 1 or FIG. 2 were to be disposed in a polymerization device, the color-temperature indicators would be directly irradiated by the radiation emitted by the energy source. The direct thermal and light radiation would influence the measurement result. In order to prevent this, for the purposes of the measurements, the polymerization temperature test element 10 is reversed so that its opening 24 is downwardly oriented. In this event, the opening 14 is, as seen in FIG. 2, open and the mass for the energy radiation is mounted in the receipt region 12.

The base element 20 can be comprised of any suitable desired material. A certain temperature stability is desired, but the production costs thereof should be kept in context. In this connection, it can be considered that such a base element can be formed of a light-shaded or colored pressed cardboard body, whereupon the light shade or light color property is preferred in order to prevent the absorption of too much radiation. It is to be understood that in lieu of such a configuration, however, any other desired different configuration can be provided such as, for example, a configuration formed of metal or formed of a temperature stable plastic or synthetic material.

Figure 3:
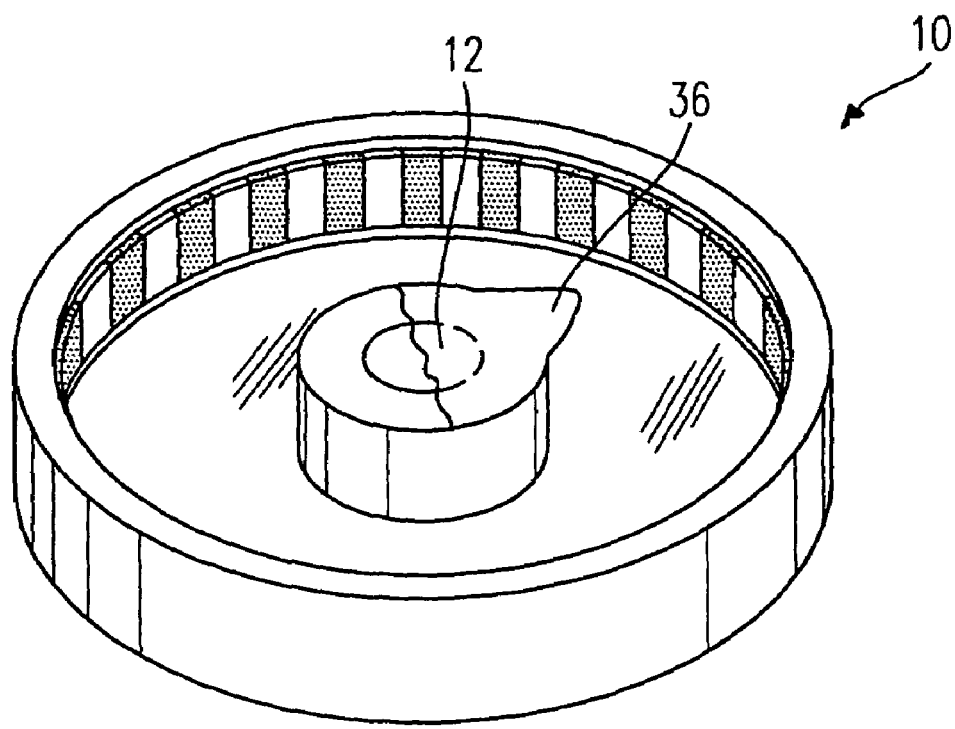
FIG. 3 is a perspective view of a second embodiment of the inventive polymerization temperature test element.
Figure 4:
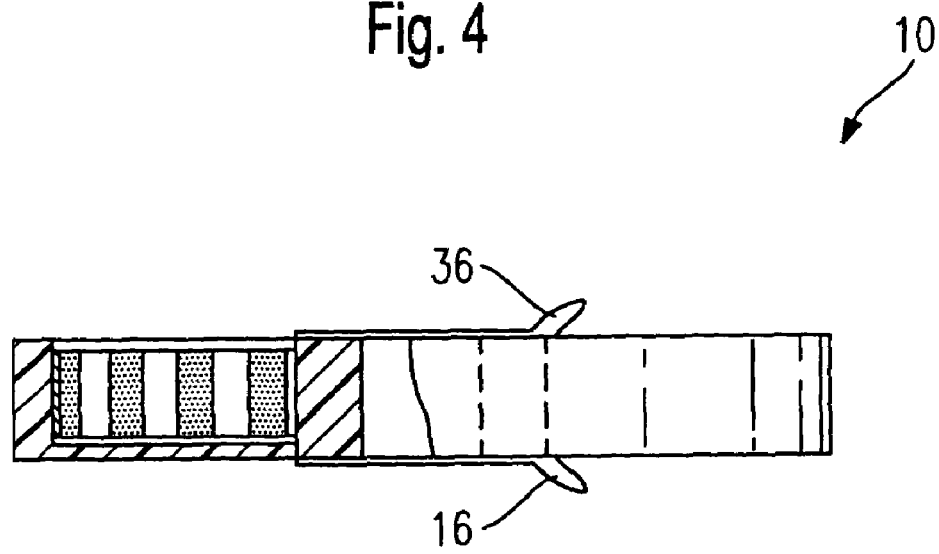
FIG. 4 is a sectional view through the second embodiment of the polymerization temperature test element shown in FIG. 3.

FIGS. 3 and 4 illustrate a second embodiment of the polymerization temperature test element 10 of the present invention. In this connection, the identical reference numerals used in FIGS. 1 and 2 are used in connection with the description of the second embodiment. The polymerization temperature test element 10 comprises, in the second embodiment, a throughbore for configuring the receipt region 12. As can be seen, two foils 16 and 36 are provided in lieu of a single foil 16 for covering the receipt region.

FIG. 5 shows a type of cover 35 for an inventive polymerization temperature test element 10 on whose outer periphery are configured color-temperature indicators 32 and 34 which are oriented inwardly. In this embodiment, the receipt region is configured underneath a through opening 38 whereat the mass to be polymerized is disposed. The energy radiation can penetrate through the opening 38 into the interior volume of the polymerization temperature test element 10—namely, into the receipt region 12. The color conversion of the color-temperature indicators is effected via the transmission of the thermal heating onto the color-temperature indicators.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A polymerization temperature test element for a polymerization device for polymerizing a dental restoration product, the polymerization device having an energy source for irradiating the dental restoration product with one or both of light radiation and thermal radiation to effect polymerization of the dental restoration product; comprising:
    a bowl shaped base element (20) having a circumferential wall (28) and a floor surface (26);
    a centrally located receipt region (12) carried by the base element (20) and extending beyond the floor surface, the receipt region being operable to receive a dental restoration product to be polymerized in response to the application of energy from the irradiating source, the base element (20) and the receipt region (12) being configured so as to be subjected to the respective light and thermal radiation emitted by the energy source to effect polymerization of the dental restoration product received by the receipt region (12), the receipt region being configured in the manner of a centrally disposed hub; and
    irreversible temperature indicating means carried by the inner side of the circumferential wall of the base element and spaced away from the receipt region a distance sufficiently great so that the temperature indicating means cannot be in contact with the dental restoration product to be polymerized, the temperature indicating means indicating that at least one discrete temperature has been reached during irradiation of the dental restoration product.

2. A polymerization temperature test element for a polymerization device for polymerizing a dental restoration product, the polymerization device having an energy source for irradiating the dental restoration product with one or both of light radiation and thermal radiation to effect polymerization of the dental restoration product; comprising:
    a bowl shaped base element (20) having a circumferential wall (28);
    a centrally located receipt region (12) carried by the base element (20) and operable to receive a dental restoration product to be polymerized in response to the application of energy from the irradiating source, the base element (20) and the receipt region (12) being configured so as to be subjected to the respective light and thermal radiation emitted by the energy source to effect polymerization of the dental restoration product received by the receipt region (12), the receipt region being configured in the manner of a centrally disposed short cylinder; and
    irreversible temperature indicating means carried by the inner side of the circumferential wall of the base element and spaced away from the receipt region a distance sufficiently great so that the temperature indicating means cannot be in contact with the dental restoration product to be polymerized, the temperature indicating means indicating that at least one discrete temperature has been reached during irradiation of the dental restoration product wherein the base element (20) includes at least one temperature indicating means (32, 34) having a color indicia, the color indicia of each color-temperature indicator (32, 34) having the characteristic that at least one of its brightness and its original color changes in an irreversible manner upon reaching a predetermined release temperature unique to the respective color-temperature indicator (32. 34).

3. A polymerization temperature test element for use with a polymerization device having an energy source for irradiating a dental restoration product; the polymerization test element comprising:
    a bowl shaped base element having a circumferential wall and a centrally located receipt region configured in the manner of a centrally disposed hub, the receipt region receiving a dental restoration product which is to be irradiated from an energy source to effect polymerization of the dental restoration product, wherein the base element includes a floor surface between the circumferential wall and the centrally disposed hub, and wherein the receipt region is disposed centrally and extends beyond the floor surface; and
    peripheral temperature indicating means supported by the inner side of the circumferential wall of the base element, the temperature indicating means being capable of indicating when at least one discrete temperature has been reached during the irradiation of the dental restoration product, the temperature indicating means being irreversible.

4. A polymerizable temperature test element for a polymerization device, in particular in the field of dental restoration, the device having an energy source for irradiating a mass, a bowl shaped base element (20) with a circumferential wall (28) and a support strip (30) which is mounted on the inner side of the circumferential wall (28) and provided with color temperature indicators (32, 34) which change colon at discrete temperatures, characterized in that:
    the base element (20) has a central region (12) in the form of an elevated hub in the shape of a short cylinder to be filled with the mass to be irradiated and that the central region (12) is spaced away from the support strip (30) a distance sufficient that the temperature indicators (32, 34) can not be in contact with the mass to be irradiated and that the temperature indicators (32,34) change the colors irreversible.

5. A test element for a polymerization device in the field of dental restoration, the device having an energy source, the test element (10) comprises a base body (20) having a receipt region (12) to be filled with the material to be hardened by the light radiation and/or thermal radiation and to be subjected to the radiation emitted by the energy source of the polymerization device, characterized in that
    the base body (20) comprises at least one temperature indicator (32,34) for measuring the hardening border of the material to be polymerized in the receipt region via the change of color of the indicator, and
    the base body (20) at least partially consist of a material not being permeable for the light, and the part of the base body (20) being nonpermeable for light is arranged between the energy source of the polymerization device and the color temperature indicators (32, 34).

* * * * *

UNITED STATES PATENT AND TRADEMARK OFFICE
CERTIFICATE OF CORRECTION

| | |
|---|---|
| PATENT NO. | : 7,445,440 B2 |
| APPLICATION NO. | : 10/622419 |
| DATED | : November 4, 2008 |
| INVENTOR(S) | : Walter Pokorny et al. |

It is certified that error appears in the above-identified patent and that said Letters Patent is hereby corrected as shown below:

Claim 4, col. 8, line 37, change "colon" to --colors--.

Signed and Sealed this

Tenth Day of February, 2009

JOHN DOLL
*Acting Director of the United States Patent and Trademark Office*